United States Patent [19]

Marcum

[11] 4,248,096
[45] Feb. 3, 1981

[54] MACHINE FOR FATIGUE TESTING OF MATERIALS

[75] Inventor: Alfred L. Marcum, Centerville, Ohio

[73] Assignee: Monsanto Research Corporation, St. Louis, Mo.

[21] Appl. No.: 49,428

[22] Filed: Jun. 18, 1979

[51] Int. Cl.³ .............................................. G01N 3/32
[52] U.S. Cl. ........................................ 73/828; 73/830
[58] Field of Search ............... 73/830, 828, 797, 810, 73/826

[56] References Cited

U.S. PATENT DOCUMENTS

| 2,533,332 | 12/1950 | Steiding | 73/828 |
| 2,595,069 | 4/1952 | Fritz | 73/797 |
| 3,049,916 | 8/1962 | Weiner | 73/828 |
| 4,030,348 | 6/1977 | Fletcher et al. | 73/810 |

Primary Examiner—Anthony V. Ciarlante
Attorney, Agent, or Firm—Jacox & Meckstroth

[57] ABSTRACT

A machine for cyclically applying a force to material specimens for testing the fatigue properties thereof. The specimens are positioned between two members, at least one of which moves angularly in a wobble type of action in a cyclic operation. Enclosure members enclose any suitable desired fluid within which the test specimens are tested.

20 Claims, 8 Drawing Figures

4,248,096

MACHINE FOR FATIGUE TESTING OF MATERIALS

BACKGROUND OF THE INVENTION

Numerous types of materials are used in such a manner as to be subject to fatigue. In some instances such materials are exposed to a specific environment.

It is an object of this invention to provide a machine for fatigue testing of materials.

It is another object of this invention to provide a machine which is particularly adapted for tensional fatigue testing of materials.

It is another object of this invention to provide such a machine which is capable of testing materials in a specific environment.

It is another object of this invention to provide such a machine which is capable of simultaneously testing a plurality of material specimens.

Other objects and advantages of this invention reside in the construction of parts, the combination thereof, the method of construction, and the mode of operation, as will become more apparent from the following description.

BRIEF SUMMARY OF THE INVENTION

The machine of this invention comprises a stationary member and a movable member. Specimens to be tested are attached to the stationary member and to the movable member. The movable member has portions which move cyclically toward and away from the stationary member, so that a specimen which extends between the two members has tensional or compressional forces applied thereto, and then such forces are removed in a cyclic manner.

Herein the movable member is operated by a rotary member, so that as the rotary member rotates, there is cyclic movement of the movable member.

The machine of this invention is provided with an enclosure member which encloses the stationary member and the movable member. The enclosure is adapted to contain fluid such as a gas or a liquid, which presents an environment in which the specimens are tested by the machine.

DETAILED DESCRIPTION OF THE INVENTION

Figure 1:
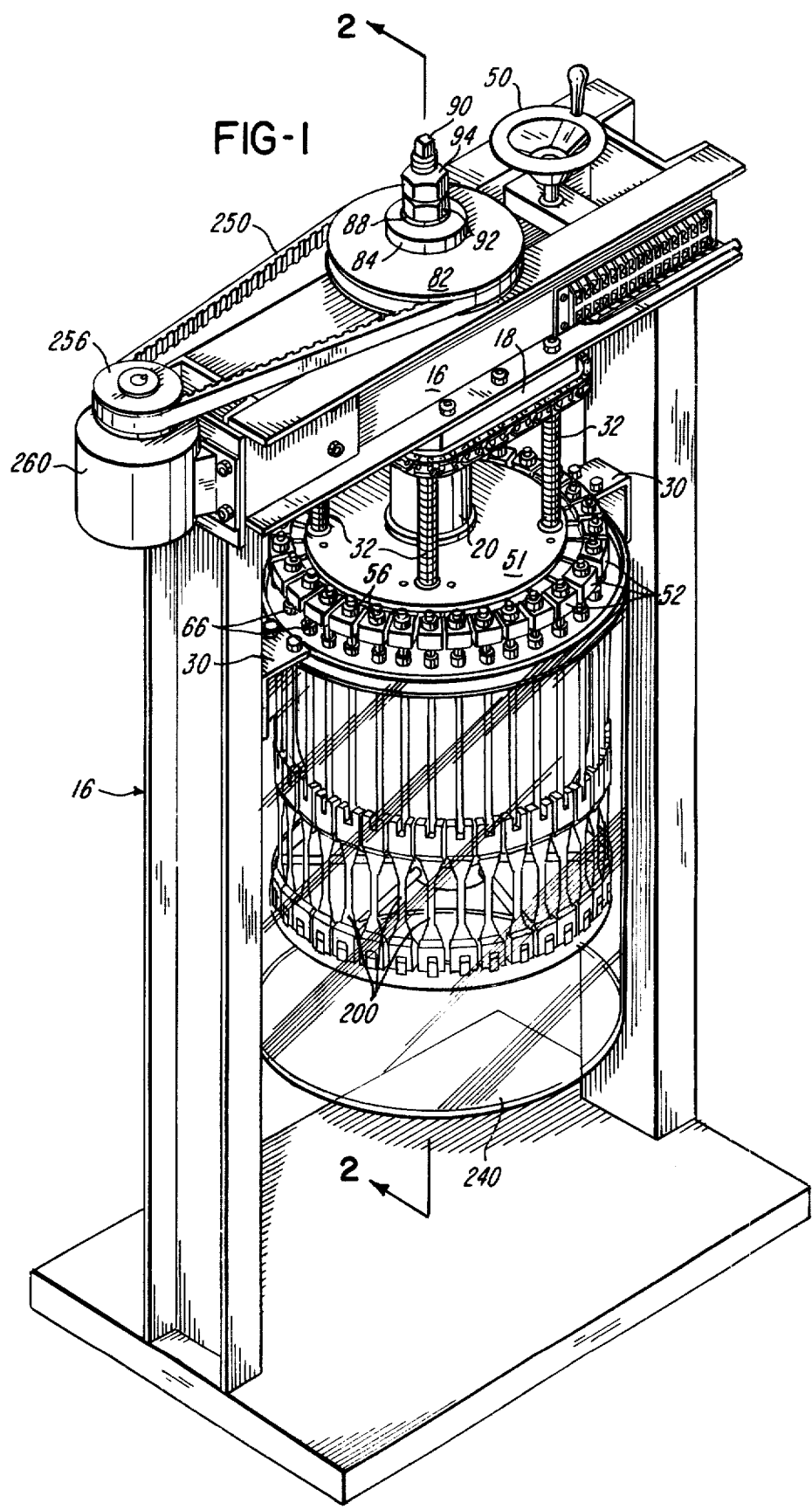
FIG. 1 is a perspective view of a machine of this invention.

A machine of this invention comprises suitable support structure 16. A mounting bracket 18 is attached to the upper portion of the support structure 16. Extending through the mounting bracket 18 and attached thereto is an elongate tube 20. Encompassing the elongate tube 20 and spaced above the lower end thereof is a platform 24 which is attached to the elongate tube 20 and is also attached to the support structure 16, by means of lugs 30.

A plurality of threaded rods 32 are journalled in the bracket 18 and in the platform 24 and extend therebetween. Attached to the upper portion of each of the threaded rods 32 for rotation thereof is a toothed sprocket 36. In meshed engagement with each toothed sprocket 36 is a drive chain 40 which is also in toothed engagement with a drive sprocket 42. The drive sprocket 42 is attached to a drive shaft 44, which is journalled in a bearing 48 which is supported by the support structure 16. The upper end of the shaft 44 has a crank 50 attached thereto for rotation of the shaft 44.

Figure 2:
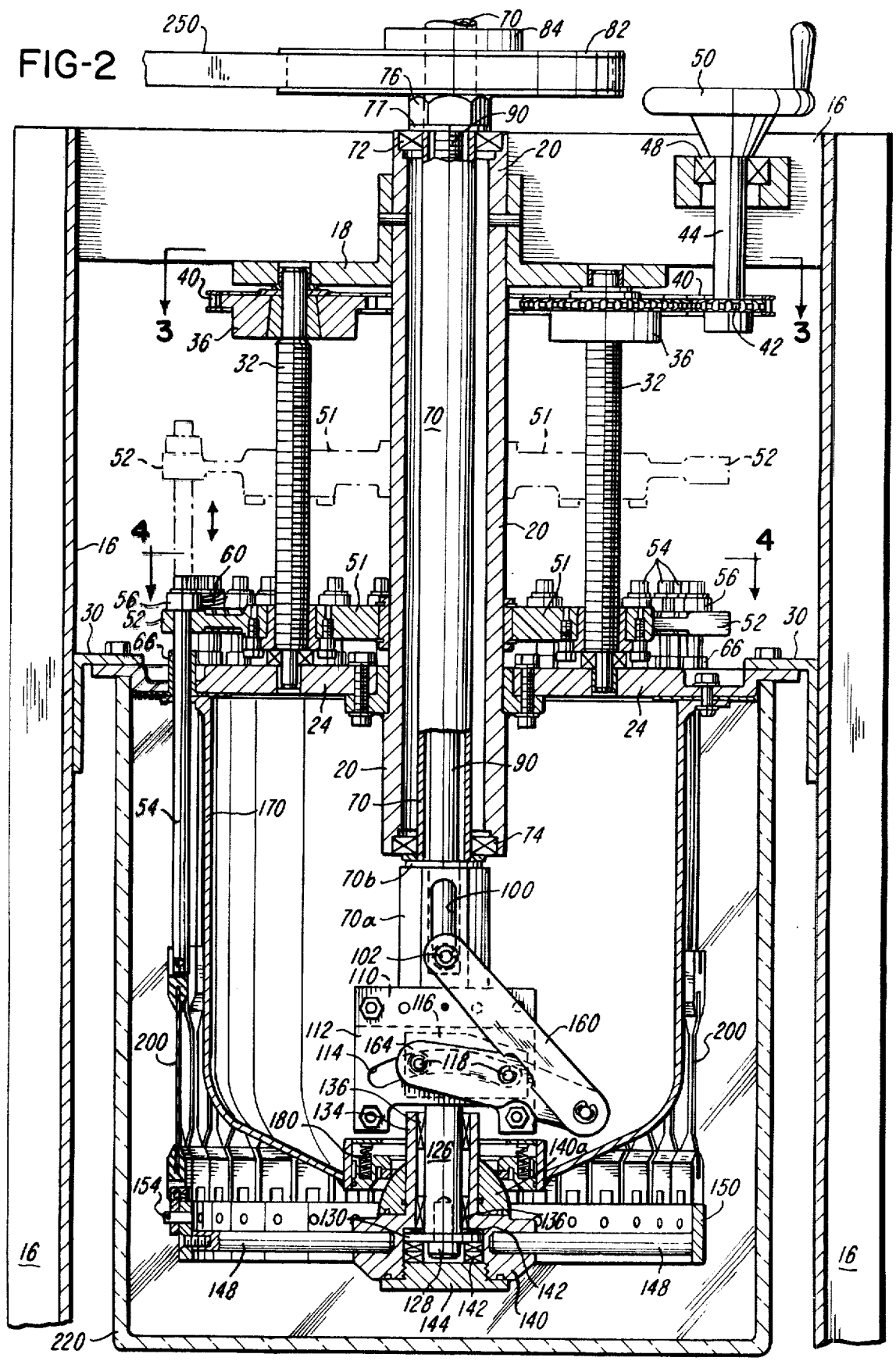
FIG. 2 is a sectional view taken substantially on line 2—2 of FIG. 1, and drawn on a larger scale than FIG. 1.
Figure 3:
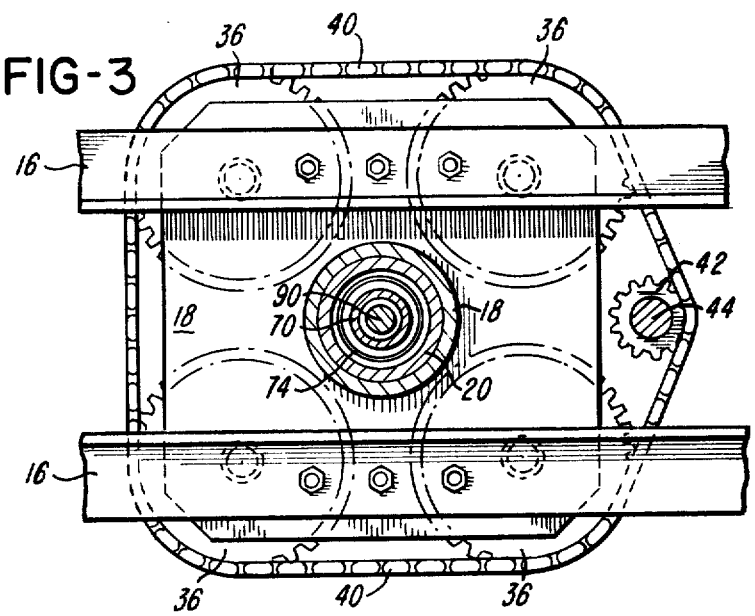
FIG. 3 is a sectional view taken substantially on line 3—3 of FIG. 2, but drawn on a slightly smaller scale than FIG. 2.
Figure 4:
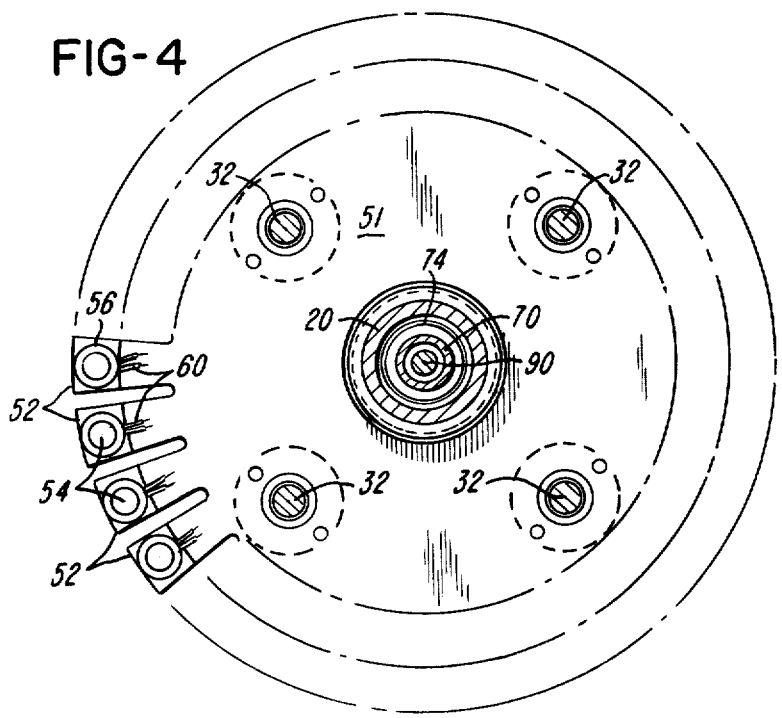
FIG. 4 is a sectional view taken substantially on line 4—4 of FIG. 2, but drawn on a slightly smaller scale than FIG. 2.

Positioned above the platform 24 is a carriage 51, through which the threaded rods 32 threadedly extend. The carriage 51 has at the periphery thereof an annularly arranged series of tabs 52. A stem 54 slidably extends through each of the tabs 52. Each stem 54 is encompassed by a sensor element 56 which is positioned upon the respective tab 52. The upper end of each stem 54 is secured in any suitable manner to maintain the upper end of the stem 54 above its respective sensor element 56. Each sensor element 56 may be any suitable pressure sensitive or force sensitive device such as a piezo-electric element or the like. Each sensor element 56 has a pair of electrical leads 60 extending therefrom, as illustrated in FIG. 2, to a connection block 64, shown in FIG. 1.

Each stem 54 extends downwardly from its respective tab 52 of the carriage 51 and slidably extends through a sleeve 66 in the platform 24.

A hollow shaft 70 extends downwardly through the elongate tube 20 and is journalled therein by a bearing 72 adjacent the upper end thereof and by a bearing 74 adjacent the lower end thereof. A nut 76 is threadedly attached to the hollow shaft 70 immediately above the bearing 72. A washer 77 separates the nut 76 from the bearing 72. Above the nut 76 is a pulley 82 which encompasses and is attached to the hollow shaft 70 for rotation thereof. Above the pulley 82 is an annular collar 84 which encompasses the hollow shaft 70 and rests upon the pulley 82. The hollow shaft 70 has the upper end thereof immediately above the collar 84 and is encompassed by an annular disc 88.

Extending through the hollow shaft 70 is a solid inner shaft 90. The upper end of the inner shaft 90 is threaded and has threadedly attached thereto nuts 92 and 94. The nut 92 engages the disc 88 and supports the shaft 90 upon the disc 88 and upon the collar 84.

The lower portion of the hollow shaft 70 has a greater diameter part 70a which has an elongate slot 100 therein. A pin 102 extends through the solid inner shaft 90 and through the slot 100 in the hollow shaft 70. The hollow shaft 70 has a shoulder 70b which is journalled upon the bearing 74.

Figure 6:
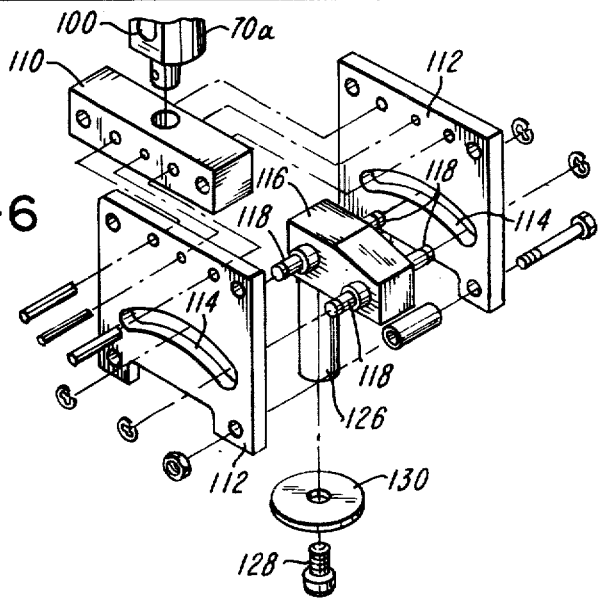
FIG. 6 is a perspective exploded view showing a portion of the machine of this invention.
Figure 7:
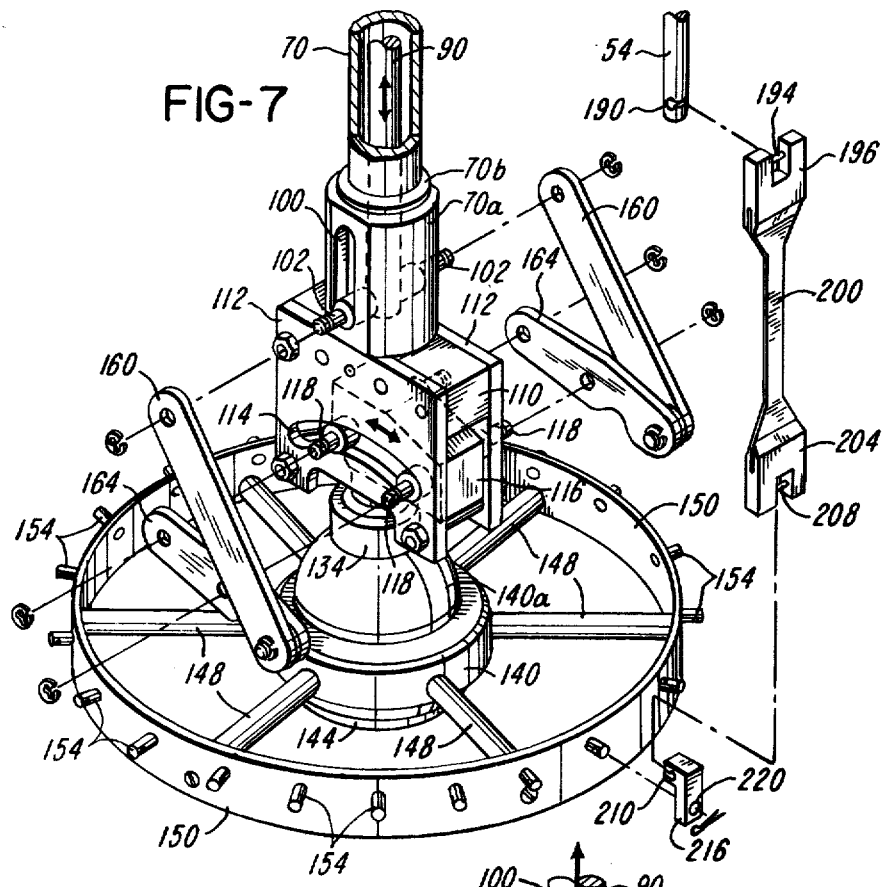
FIG. 7 is a perspective exploded view with parts shown in section, showing a portion of the machine of this invention.

As best shown in FIGS. 6 and 7, attached to the lower end of the greater diameter part 70a of the hollow shaft 70, is a spacer member 110 which separates a pair of plates 112 at the upper portion thereof. Each of the plates 112 has an arcuate slot 114 therein. Between the plates 112 below the spacer member 110 is a block 116. A plurality of pin members 118 extend through the block 116 and through the slots 114 in the plates 112. The pin members 118 are secured within the block 116 and are slidably movable within the arcuate slots 114 of the plates 112.

Figure 8:
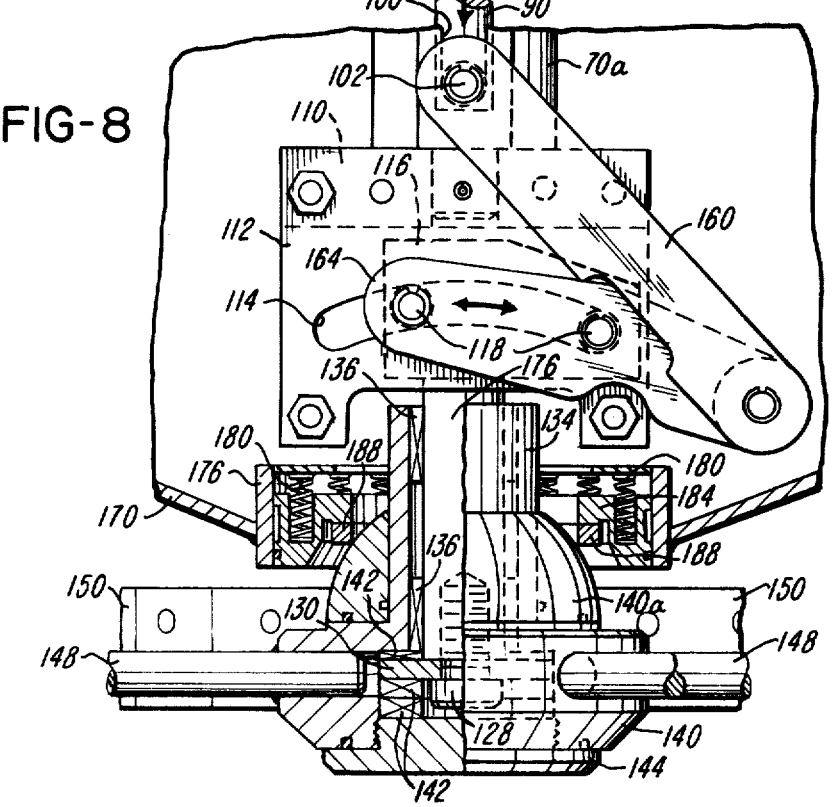
FIG. 8 is a side sectional view, with parts broken away, showing a portion of the machine as illustrated in FIG. 7, but drawn on a larger scale than FIG. 7.

The block 116 has a stub shaft 126 secured thereto and extending downwardly therefrom. Attached to the lower end of the stub shaft 126 by means of a bolt 128 is a bearing plate 130. A sleeve 134, best shown in FIGS. 2 and 8, encompasses the stub shaft 126, with bearing members 136 separating the stub shaft 126 from the sleeve 134. Attached to the sleeve 134 is a housing or hub 140 having an arcuate dome portion 140a. Within the housing 140 are bearing members 142, which separate the housing 140 from the bearing plate 130. A cap 144 at the lower portion of the housing 140 encloses the housing 140 and retains the position of the bearings 142.

Attached to the housing 140 and extending therefrom are a plurality of arms 148 to which is attached a ring 150. The ring 150 has secured thereto a plurality of connector fingers 154, as best shown in FIG. 7.

As previously discussed and as best shown in FIG. 7, the pin 102 extends through the solid inner shaft 90 and through the slot 100 in the greater diameter part 70a of the hollow shaft 70. Pivotally attached to the pin 102 at opposite ends thereof are links 160. Also pivotally attached to each of the links 160 is a lever 164. Each lever 164 is pivotally attached to the block 116 by the pins 118 which extend through the block 116 and through the arcuate slots 114 in the plates 112.

Figure 5:
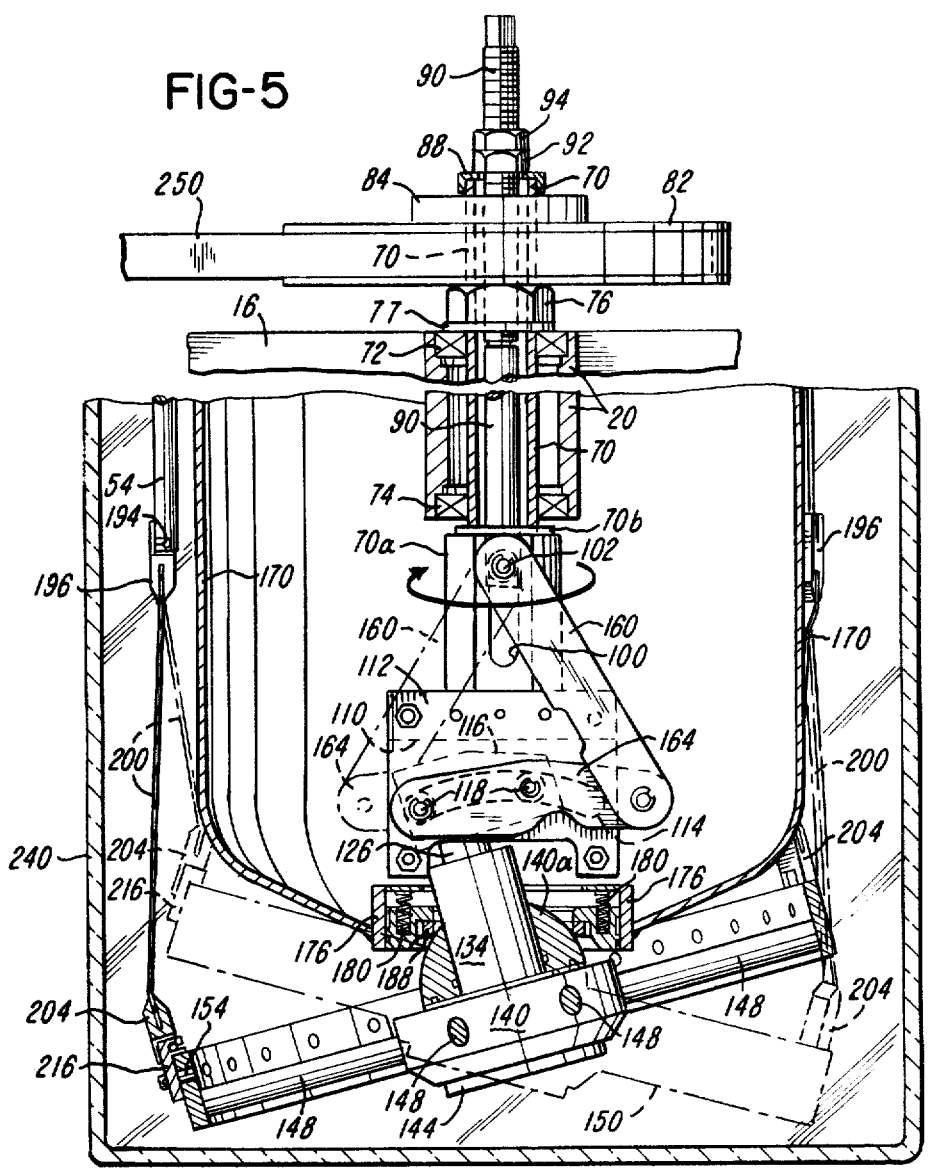
FIG. 5 is a fragmentary sectional view, with parts broken away, showing a portion of the machine as illustrated in FIG. 2 and showing parts thereof in another position of operation.

An inner enclosure 170, best shown in FIGS. 2 and 5, has the upper portion thereof attached to the platform 24 in any suitable manner. The inner enclosure 170 encompasses the lower portion of the elongate tube 20, the hollow shaft 70 and the inner shaft 90. The inner enclosure 170 also encompasses the links 160 and the levers 164. The lower portion of the inner enclosure 170 is adjacent the arcuate dome portion 140a of the housing 140. Attached to the inner enclosure 170 and encompassing the sleeve 134 is a holder 176. Within the holder 176 is a plurality of spring members 180 which engage a retainer 184. The retainer 184 has attached thereto an annular sealing member 188, which is in engagement with the arcuate dome portion 140a of the housing 140.

The stems 54, discussed above, are exterior of the inner enclosure 170. The lower portion of each stem 54, as best illustrated in FIG. 7, is provided with a slot 190 which is adapted to receive a pin 194, which is a part of a clasp 196. Attached to each clasp 196 is a test specimen 200. The test specimen 200 is also attached to a clasp 204 which has a pin 208 which is positioned in a slot 210 in a connector 216. Each connector 216 has an opening 220 therein which receives one of the connector fingers 154. Thus, each test specimen 200 is effectively positioned between the lower portion of a stem 54 and a connector finger 154 which is attached to the ring 150. There is thus an annularly arranged set of specimens 200 immediately exterior of the inner enclosure 170.

Also attached to the platform 24 by any suitable means is an outer enclosure 240 which encompasses the stems 54, the specimens 200, the inner enclosure 170, the ring 150, and elements associated therewith, as best shown in FIG. 2.

The pulley 82, at the upper portion of the shafts 70 and 90, is encompassed by a continuous belt 250. The belt 250 also encompasses a pulley 256 of a drive motor 260, which is attached to the upper portion of the support structure 16, as shown in FIG. 1.

Operation

The drive motor 260, through the belt 250 rotates the shafts 70 and 90. Thus, the plates 112, below the shafts 70 and 90, rotate. The block 116, positioned between the plates 112, is also rotated. Thus, the stub shaft 126, which is attached to the block 116, also rotates. Therefore, the bearing plate 130 rotates. However, the housing 140 does not rotate, and thus, there is relative rotative movement between the bearing plate 130 and the bearings 142.

FIG. 2 shows the stub shaft 126 coaxial with the shafts 70 and 90. However, in order to apply forces cyclically to the test specimens 200, the stub shaft 126 is adjusted with respect to the shafts 70 and 90 to provide an angular relationship therebetween. The nuts 92 and 94, best shown in FIGS. 1 and 5, are rotated with respect to the shaft 90 for axial movement of the shaft 90 with respect to the shaft 70. When this axial movement of the shaft 90 occurs, the pin 102 is drawn along the slot 100 from the position thereof illustrated in FIGS. 2, 7 and 8 to the position thereof shown in FIG. 5. When this movement of the pin 102 occurs, the link 160 and the lever 164 are pivotally moved. When the lever 164 is pivotally moved the pins 118 are moved along the arcuate slots 114 of the plates 112, and the block 116 is moved in its position between the plates 112. When the block 116 is moved, the stub shaft 126 is angularly moved to a position such as that illustrated in FIG. 5.

In such a position, the stub shaft 126 is angular with respect to the shafts 70 and 90. When the stub shaft 126 is so angularly inclined, rotation of the shafts 70 and 90 causes rotative movement of the stub shaft 126 about its own longitudinal axis and also causes angular movement of the stub shaft 126 about a point which is coaxial with the axis of rotation of the shafts 70 and 90. Such angular movement of the stub shaft 126 may be described as generating a cone. Therefore, rotation of the bearing plate 130 within the housing or hub 140 causes the housing or hub 140 and the elements joined thereto to oscillate or move angularly or wobble, as illustrated in FIG. 5. As the housing 140 moves angularly as illustrated in FIG. 5, the ring 150 moves angularly in a wobble or oscillating type of action. When this wobble action occurs, the test specimens 200 which extend between the ring 150 and the stems 54 are cyclically placed in tension and then relaxed. Thus, fatigue testing of the specimens 200 occurs. The frequency of this cyclic movement, of course, depends upon the rate of rotation of the shafts 70 and 90.

The tensional forces applied to the test specimens 200 are adjustable by rotation of the crank 50, which rotates the chain 40, causing rotation of the threaded rods 32. Rotation of the threaded rods 32 raises or lowers the carriage 51, as illustrated in FIG. 2, and the stems 54 move upwardly or downwardly with such movement of the carriage 51. Movement of the stems 54 changes the tension applied to the test specimens 200.

Any suitable fluid, a gas or a liquid, may be contained between the outer enclosure 240 and the inner enclosure 170. Thus, the test specimens 200 may be tested in any desired environment.

When a test specimen 200 falls in fatigue, the forces applied to the respective stem 54 changes. This change in force is sensed by the respective sensor element 56 which provides a signal in regard thereto.

It is to be understood that a machine of this invention may be employed to apply compressional forces, rather than tensional forces, to test specimens.

Although the preferred embodiment of this invention has been described, it will be understood that within the purview of this invention various changes may be made in the form, details, proportion and arrangement of parts, the combination thereof, and the mode of operation, which generally stated consist in a machine for fatigue testing of materials within the scope of the appended claims.

The invention having thus been described, the following is claimed:

1. A machine for testing the fatigue properties of a specimen comprising:
   drive means rotating about a given axis,
   rotary means, the rotary means having a first portion a second portion, the first portion of the rotary means being within the axis of rotation of the drive means, the second portion of the rotary means being in spaced relationship from the axis of rotation of the drive means,
   connector means joining the drive means to the second portion of the rotary means for rotation of the rotary means with rotation of the drive means,
   first attachment means, the first attachment means being joined to the rotary means and having a given angular relationship with respect thereto, the first attachment means being joined to the rotary means for relative rotational movement between the first attachment means and the rotary means while maintaining the given angular relationship with regard thereto,
   second attachment means, the second attachment means being stationary and in spaced relationship from the first attachment means,
   securing means for joining a plurality of specimens to the first attachment means and to the second attachment means, as the specimens are in given positions and extend between the first attachment means and the second attachment means,
   the drive means rotating the rotary means, rotation of the rotary means thus causing angular oscillating movement of the first attachment means with respect to the second attachment means, the specimens thus being cyclically placed in tension as the specimens remain in the given positions thereof.

2. The machine of claim 1 which includes means for adjusting the spaced relationship between the second portion of the rotary means and the axis of rotation of the drive means, to adjust the angle of the oscillating movement of the first attachment means with respect to the stationary second attachment means.

3. The machine of claim 1 which includes means for adjusting the spaced relationship between the first attachment means and the stationary second attachment means for adjusting the tensional forces applied to the specimens.

4. The machine of claim 1 which includes enclosure means enclosing the securing means for enclosing the specimens in a desired environment during testing thereof.

5. The machine of claim 1 in which the first attachment means and the second attachment means are adapted to retain a plurality of elongate specimens in closely spaced substantially annular parallel relationship.

6. The machine of claim 1 which includes means sensing the presence of tensional forces applied to the specimens.

7. A machine for testing fatigue properties of specimens of elastomeric material comprising:
   a tubular rotatable drive member,
   a shaft within the tubular rotary drive member and axially movable with respect thereto,
   a first lever and a second lever, one end portion of the first lever being pivotally attached to the shaft and the other end portion of the first lever being pivotally attached to one end portion of the second lever,
   a coupling attached to the tubular rotatable drive member and rotatable therewith, the coupling having a cavity therein and an arcuate slot leading to the cavity,
   a connector member within the cavity of the coupling and movable with respect thereto,
   pin means extending through the arcuate slot and joining the second lever to the connector member,
   stationary support means,
   a carrier member pivotally supported by the stationary support means,
   a stub shaft attached to the connector member and rotatable within the carrier member,
   the carrier member having laterally extending attachment portions,
   attachment means carried by the stationary support means and in spaced relationship from the attachment portions of the carrier member,
   means for attaching specimens for test to the attachment means of the stationary support means and to the attachment portions of the carrier member,
   the lever members angularly moving the carrier member to desired positions with respect to the axis of rotation of the tubular rotatable drive member as the shaft is moved axially with respect to the tubular rotatable drive member,
   the carrier member when angular with respect to the axis of rotation of the tubular rotatable drive member having an oscillating motion during rotation of the tubular rotatable drive member,
   the specimens thus being cyclically placed in tension as rotation of the tubular drive member occurs.

8. The machine of claim 7 in which the attachment means carried by the stationary support means includes a carriage, the carriage being movable toward and away from the attachment portions of the carrier member, the cyclic tensional forces applied to specimens thus being adjusted by movement of the carriage with respect to the carrier member.

9. Apparatus for fatigue testing a specimen of material comprising:
   a pair of coaxial rotary shafts,
   means for rotation of the rotary shafts,
   means for relative axial movement between the shafts,
   pivotally movable attachment means,
   connection means joining the shafts to the pivotally movable attachment means for pivotal adjustment of the pivotally movable attachment means with relative axial movement between the shafts, the connection means also joining the shafts to the pivotally movable attachment means for rotation of the pivotally movable attachment means with rotation of the shafts, the pivotally movable attachment means thus being angularly movable in a wobble action with rotation of the shafts, stationary attachment means, means for attachment of a plurality of specimens to the stationary attachment means and to the pivotally movable attachment means, the specimens thus having forces applied thereto sequentially and cyclically with wobble action of the pivotally movable attachment means with rotation of the rotary shafts.

10. The machine of claim 9 in which the attachment means includes means for attaching a plurality of specimens in an annular arrangement.

11. The machine of claim 9 which includes sensing means sensing the presence of forces applied to the specimens.

12. Apparatus for fatigue testing a specimen of material comprising:

a rotary shaft, means for rotation of the rotary shaft, pivotally movable attachment means, means for pivotal adjustment of the pivotally movable attachment means with respect to the axis of rotation of the rotary shaft, means joining the rotary shaft to the pivotally movable attachment means for angular movement of the pivotally movable attachment means and for relative rotational movement between the pivotally movable attachment means and the rotary shaft with rotation of the rotary shaft, the pivotally movable attachment means thus being angularly movable in a wobble action with rotation of the rotary shaft, second attachment means, the second attachment means being stationary, means for attachment of a plurality of specimens to the second attachment means and to the pivotally movable attachment means, the specimens thus having forces applied thereto sequentially and cyclically with wobble action of the pivotally movable attachment means with rotation of the rotary shaft.

13. A machine for fatigue testing of a specimen comprising:

a first shaft, the first shaft rotating about the longitudinal axis thereof, a second shaft, the second shaft having an axial portion thereof coincident with the axis of rotation of the first shaft, the second shaft having its longitudinal axis angular with respect to the longitudinal axis of the first shaft, the second shaft being pivotally movable about said axial portion, means connecting the second shaft to the first shaft for pivotal movement of the second shaft with rotation of the first shaft, first attachment means, the first attachment means being stationary, second attachment means spaced from the first attachment means, means connecting the second attachment means to the second shaft in a given angular relationship with regard thereto, and means for attaching a plurality of specimens to the first attachment means and to the second attachment means for cyclically applying forces to the specimens with rotation of the first shaft and with pivotal movement of the second shaft.

14. The machine of claim 13 in which the pivotal movement of the second shaft is angular movement which generates a generally conical path.

15. A machine for fatigue testing of a specimen comprising:

a first rotary shaft, the first rotary shaft rotating about the longitudinal axis thereof, a second rotary shaft, the second rotary shaft having an axial portion thereof coincident with the axis of rotation of the first rotary shaft, the second rotary shaft having its longitudinal axis angular with respect to the longitudinal axis of the first rotary shaft, first connector means, the first connector means connecting the second rotary shaft to the first rotary shaft for pivotal movement of the second rotary shaft in a conical path about said point which is coaxial with the axis of rotation of the first rotary shaft and for rotative movement of the second rotary shaft about its own longitudinal axis, first attachment means, the first attachment means being stationary, second attachment means, the second attachment means being in spaced relationship from the first attachment means, second connector means, the second connector means connecting the second attachment means to the second rotary shaft in a given angular relationship with regard thereto and for relative rotative movement between the second attachment means and the second rotary shaft, and means for attaching a plurality of specimens to the first attachment means and to the second attachment means for sequentially and cyclically applying forces to the specimens with rotation of the first rotary shaft and the second rotary shaft.

16. The machine of claim 15 which includes means for adjusting the spaced relationship between the first attachment means and the second attachment means.

17. The machine of claim 15 which includes means for adjusting the angular relationship of the longitudinal axis of the second rotary shaft with respect to the longitudinal axis of the first rotary shaft.

18. The machine of claim 15 in which the second attachment means includes an annular member and means for attaching the specimens to the annular member.

19. The machine of claim 15 which includes enclosure means enclosing the first rotary shaft, the second rotary shaft, the first connector means, the second connector means, the first attachment means, and the second attachment means, for testing specimens in a given desired environment.

20. A machine for testing the fatigue properties of material specimens comprising:

drive means rotating about a given axis, rotary means, the rotary means having an axis of rotation which is coaxial with the axis of rotation of the drive means, means joining the drive means to the rotary means for rotative movement of the rotary means and for angular movement of the rotary means about the axis of rotation of the drive means, the angular movement of the rotary means being such as to generate a cone with rotation of the drive means, first attachment means, the first attachment means being movable and joined to the rotary means for relative rotational movement between the first attachment means and the rotary means and for wobble movement of the first attachment means with rotational movement of the rotary means, second attachment means, the second attachment means being stationary and in spaced relationship from the first attachment means, securing means for joining a plurality of specimens to the movable first attachment means and to the stationary second attachment means, rotation of the drive means thus rotating the rotary means, rotation of the rotary means causing wobble movement of the first attachment means with respect to the stationary second attachment means, and thus sequentially and cyclically placing the specimens in tension.

* * * * *